(12) United States Patent
Kim et al.

(10) Patent No.: US 9,220,570 B2
(45) Date of Patent: Dec. 29, 2015

(54) AUTOMATED SURGICAL AND INTERVENTIONAL PROCEDURES

(71) Applicant: Children's National Medical Center, Washington, DC (US)

(72) Inventors: Peter C. Kim, Washington, DC (US); Axel Krieger, Alexandria, VA (US); Yonjae Kim, Falls Church, VA (US); Azad Shademan, Washington, DC (US); Simon Leonard, Washington, DC (US)

(73) Assignee: Children's National Medical Center, Washington, DC (US)

( * ) Notice: Subject to any disclaimer, the term of this patent is extended or adjusted under 35 U.S.C. 154(b) by 0 days.

(21) Appl. No.: 13/931,371

(22) Filed: Jun. 28, 2013

(65) Prior Publication Data

US 2014/0005684 A1 Jan. 2, 2014

Related U.S. Application Data

(60) Provisional application No. 61/666,399, filed on Jun. 29, 2012.

(51) Int. Cl.
*A61B 19/00* (2006.01)
*A61B 17/04* (2006.01)
(Continued)

(52) U.S. Cl.
CPC ......... *A61B 19/2203* (2013.01); *A61B 17/0469* (2013.01); *A61B 17/0643* (2013.01); *A61B 17/1285* (2013.01); *A61B 19/5212* (2013.01); *A61B 2017/1103* (2013.01); *A61B 2017/1132* (2013.01); *A61B 2019/2207* (2013.01); *A61B 2019/2292* (2013.01); *A61B 2019/5265* (2013.01); *A61B 2019/547* (2013.01)

(58) Field of Classification Search
USPC .............................. 600/424, 476; 606/1, 130
See application file for complete search history.

(56) References Cited

U.S. PATENT DOCUMENTS 6,460,810 B2 10/2002 James
7,008,373 B2 3/2006 Stoianovici et al.
(Continued)

OTHER PUBLICATIONS

G. P. Moustris, et al.; "Evolution of Autonomous and Semi-Autonomous Robotic Surgical Systems: A Review of the Literature"; The International Journal of Medical Robotics and Computer Assisted Surgery; 2011; Int J Med Robot 7, No. 4; pp. 375-392.

(Continued)

*Primary Examiner* — William Thomson
*Assistant Examiner* — Jeffrey Lipitz
(74) *Attorney, Agent, or Firm* — Oblon, McClelland, Maier & Neustadt, L.L.P

(57) ABSTRACT

Described herein are an apparatus and methods for automating subtasks in surgery and interventional medical procedures. The apparatus consists of a robotic positioning platform, an operating system with automation programs, and end-effector tools to carry out a task under supervised autonomy. The operating system executes an automation program, based on one or a fusion of two or more imaging modalities, guides real-time tracking of mobile and deformable targets in unstructured environment while the end-effector tools execute surgical interventional subtasks that require precision, accuracy, maneuverability and repetition. The apparatus and methods make these medical procedures more efficient and effective allowing a wider access and more standardized outcomes and improved safety.

26 Claims, 13 Drawing Sheets

(51) Int. Cl.
*A61B 17/128* (2006.01)
*A61B 17/064* (2006.01)
*A61B 17/11* (2006.01)

(56) References Cited

U.S. PATENT DOCUMENTS

| | | | |
|---|---|---|---|
| 8,046,054 | B2 | 10/2011 | Kim et al. |
| 8,107,717 | B2 | 1/2012 | Maeda et al. |
| 8,182,494 | B1 | 5/2012 | Yencho et al. |
| 8,196,870 | B2 | 6/2012 | Gryniewski et al. |
| 8,197,507 | B2 | 6/2012 | Garcia et al. |
| 8,792,963 | B2* | 7/2014 | Zhao et al. .............. 600/424 |
| 2001/0025183 | A1* | 9/2001 | Shahidi .............. 606/130 |
| 2006/0211604 | A1* | 9/2006 | Mentzer .............. 514/8 |
| 2007/0239028 | A1 | 10/2007 | Houser et al. |
| 2008/0138289 | A1* | 6/2008 | Goronkin et al. .............. 424/9.4 |
| 2009/0088773 | A1* | 4/2009 | Zhao et al. .............. 606/130 |
| 2009/0228019 | A1 | 9/2009 | Gross et al. |
| 2010/0256504 | A1* | 10/2010 | Moreau-Gaudry et al. .. 600/476 |
| 2011/0015649 | A1 | 1/2011 | Anvari et al. |
| 2011/0082369 | A1 | 4/2011 | Mohr et al. |
| 2011/0257661 | A1 | 10/2011 | Choi et al. |
| 2013/0123801 | A1* | 5/2013 | Umasuthan et al. .......... 606/130 |
| 2013/0169423 | A1* | 7/2013 | Iorgulescu et al. ........ 340/407.1 |
| 2013/0317344 | A1* | 11/2013 | Borus et al. ................... 600/411 |

OTHER PUBLICATIONS

Henry C. Lin, et al.; "Automatic Detection and Segmentation of Robot-Assisted Surgical Motions"; Medical Image Computing and Computer-Assisted Intervention (MICCAI); 2005; Springer: Berlin; pp. 802-810.

Carol E. Reiley, et al.; "Motion Generation of Robotic Surgical Tasks: Learning From Expert Demonstrations"; $32^{nd}$ Annual International Conference of the IEEE EMBS, Buenos Aires, Argentina; Aug. 31-Sep. 4, 2010; pp. 967-970.

R. Bauernschmitt, et al.; "Towards Robotic Heart Surgery: Introduction of Autonomous Procedures into an Experimental Surgical Telemanipulator System"; Int J Medical Robotics and Computer Assisted Surgery; 2005; pp. 74-79.

Omid Majdani, et al.; "A Robot-Guided Minimally Invasive Approach for Cochlear Implant Surgery: Preliminary Results of a Temporal Bone Study"; Int J Comput Assist Radiolsurg (CARS); 2009; pp. 475-486.

International Search Report dated Mar. 18, 2014, in International Application No. PCT/US13/48911, filed Jul. 1, 2013.

Written Opinion dated Mar. 18, 2014, in International Application No. PCT/US13/48911, filed Jul. 1, 2013.

* cited by examiner

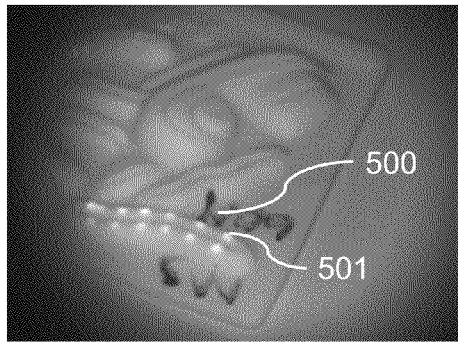 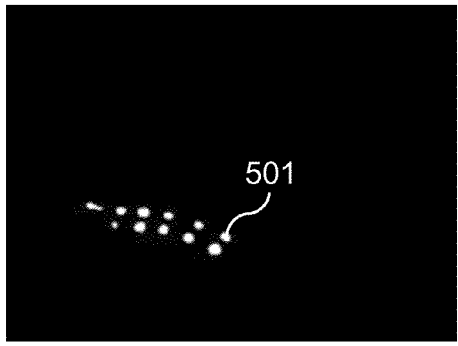
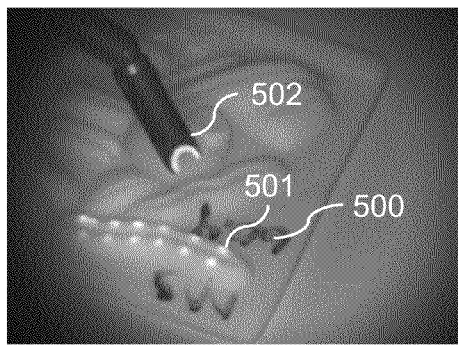 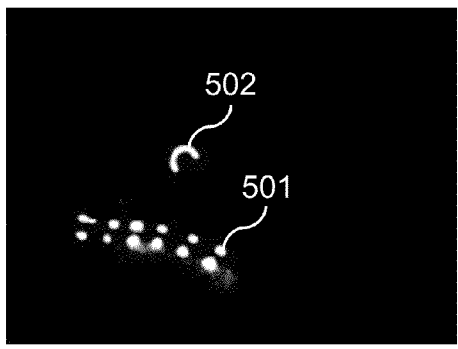
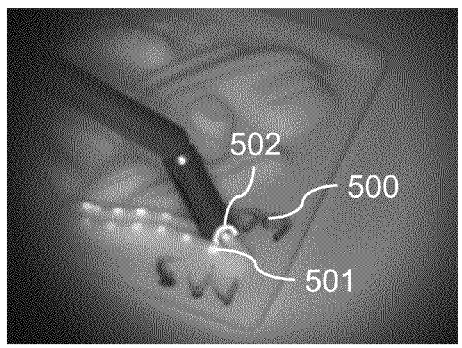 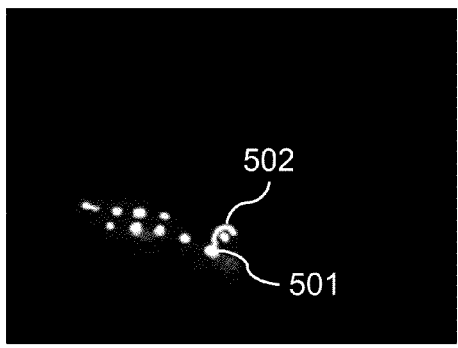
*Fig.5A*        *Fig.5B*

AUTOMATED SURGICAL AND INTERVENTIONAL PROCEDURES

CROSS-REFERENCE TO RELATED APPLICATIONS

This application claims the benefit of priority under 35 U.S.C. §119(e) from U.S. Ser. No. 61/666,399, filed Jun. 29, 2012, the entire contents of which are incorporated herein by reference.

BACKGROUND OF THE INVENTION

1. Field of the Invention

This invention is related to the field of robotic surgery, namely, full or partial automation of surgical tasks.

2. Description of the Related Art

What is available in the market as so called "robotic surgery" is typically robot-assisted surgery because the surgeon and the robot interact through a master-slave paradigm. The slave robot is constrained to follow direct commands from the surgeon master with little autonomy. While this method is reliable, it constrains the speed and dexterity of the slave robot to that of the surgeon. None of the currently available invasive surgical systems utilize true automation during the procedure. Moreover, no previous approach combines both visible light images with other modalities to control the robot.

SUMMARY OF THE INVENTION

The currently available master-slave mode of operation limits the robot to the operating surgeon's dexterity and skill, which may be inefficient for certain subtasks that require high precision, dexterity, and repetition (e.g. suturing) when compared to autonomous control. Moreover, supervised automation improves on limitations of each individual surgeon's experience-based adaptive and visual processing ability with an evidence-based decision support algorithm built on master surgeon's ability and sub-surface tissue information from a secondary imaging source.

Surgical subroutines that require high dexterity, precision, and repetition will be identified and chosen for automation. Clinical data (visual recording, robot movement, patient outcome, etc.) from both manual and robot-assisted performances of these routines by expert surgeons will be analyzed to identify the automation-critical information (e.g. key reference points, visual references, organ/vessel location/movement, etc.) and the optimal movement pattern for automation. The automation program will be designed so that the automation program can adapt the surgical task to different patients given the aforementioned critical information. The automated routine will not only mimic the clinical data, but also learn from expert surgeons' performances and improve upon the surgeons' performance to take advantage of the efficiency and effectiveness of the robot.

The automation program may make use of visual servoing with real-time visual feedback from one or more cameras, either endoscopic or externally mounted, which are capable of providing visible and/or non-visible spectrum images. An example of non-visible spectrum image is the near-infrared fluorescent (NIR) image. 3D information may be provided along with visual information through a dedicated sensor or extraction from visual information. For example, if two cameras are used, 3D depth information could be extracted from stereo triangulation algorithm. 3D depth information could also be obtained through structured-light 3D scanners, or through light-field cameras.

Due to the often dynamic and unstructured nature of the surgical environment, optical data alone may not be sufficient for robust real-time, high fidelity tracking of mobile and deformable targets; therefore, the visual data may be augmented, fused or accompanied by other sensors as needed (e.g. infrared-camera, haptic sensor, etc.). The visual image, along with other sensory and critical data, will be fed into the automation program's control system that will move the robot and the tools to perform the desired surgical task. More than one automation program may be generated for each surgical procedure, with each program accepting different combination of sensors and critical data to accommodate different surgery conditions, but accomplishing the same surgical goal. A single program may be made to accept multiple combinations of sensors and data as well.

During surgery, the robot will be able to operate under one of three modes of operations: master-slave, semi-autonomous, and supervised autonomous. In master-slave mode, the surgeon directly controls the robot's motions to perform tasks that cannot be done with the other two modes such as preparing the surgical scene for an autonomous program (e.g. placing tissue markers). In the semi-autonomous mode, the surgeon will provide the robot with action commands (e.g. place suture in specific location, cut tissue in a line, tie a knot) that the robot will perform using autonomously calculated trajectories and tool actuations. That is, after preparation of surgical site, the surgeon is still involved in decision making and command specification interactively. This interaction may be implemented through a graphical user interface, where the surgeon outlines suture locations such that the program can visually track target locations and generate robot trajectories to reach the targets. The part where the surgeon interacts with the program defines semi-autonomy. In the supervised autonomous mode, the surgeon only provides the robot with an overall goal (e.g. perform anastomosis) and the autonomous program determines the actions necessary to complete the goal (e.g. location, number, tension, and order of sutures to place) without any input from the surgeon. That is, after preparation of the surgical site, the program picks the target location and proceeds automatically. The surgeon's role is primarily safety supervision. Throughout the surgery, the surgeon may employ any of these three modes as appropriate, and at any time in the operation, the surgeon may interrupt the robot's motion and take master-slave control of the robot.

An example of one surgical subtask that embodiments of this invention could significantly benefit is anastomosis. Anastomosis is conventionally performed manually or more recently using robots through master-slave control, but both techniques are time consuming and cumbersome due to the high amount of dexterity, precision, and repetition required for the procedure. There is great potential improvement to be had from automating this task because of these characteristics.

The present technology has the potential to improve upon other surgical procedures requiring precision, repetition, maneuverability, and reproducibility, including but not limited to placement (screwing/fixation) of bone implants, tissue dissections, biopsies, vitreo-retinal surgeries, microsurgical and/or vascular anastomosis, brachytherapy, and skin closure.

Embodiments disclosed herein provide for a system for performing an automated surgical procedure. The system includes a sensor that provides information regarding a surgical field, a user interface configured to receive commands issued by a surgeon, a feedback device configured to relay information to the surgeon, a surgical tool having an end portion used for performing a surgical task, a surgical robot that is coupled to the surgical tool and that positions and orients the surgical tool, a track processing module implemented by processing hardware and configured to receive sensor data from the sensor, identify positions in at least one of a target tissue, surrounding tissues and the surgical tool end portion based on the sensor data, track the identified positions in at least one of the target tissue, the surrounding tissues and the tool end effector, and a control module implemented by the processing hardware and configured to process data received from the sensor, the track processing module, and the user interface via an automation program, to generate and send commands to the surgical robot.

According to another embodiment of the system, the system further comprises a plurality of sensors that provide information regarding the surgical field.

According to another embodiment of the system, the sensor is one of a camera, a near-infrared fluorescent (NIR) camera, a depth camera, a structured light 3D scanner.

According to another embodiment of the system, the feedback device is a display configured to show visual cues or images or an auditory device.

According to another embodiment of the system, the track processing module is further configured to track the identified positions in at least one of the target tissue, the surrounding tissues and the tool end effector, using near-infrared fluorescent (NIR) markers.

According to another embodiment of the system, the surgical robot that is detachably coupled to the surgical tool.

According to another embodiment of the system, the surgical robot is coupled to a movement mechanism that moves the surgical robot in and out of the surgical field.

According to another embodiment of the system, the automation program is semi-autonomous.

According to another embodiment of the system, the automation program is supervised autonomous.

According to another embodiment of the system, the control module is configured to disable the automation program and implement a master-slave mode.

According to another embodiment of the system, the control module is configured to interrupt the automation program based on surgeon input.

According to another embodiment of the system, the control module is further configured to implement visual servoing correction.

According to another embodiment of the system, the automation program is configured to implement anastomosis.

According to another embodiment of the system, the control module is further configured to further generate the commands based on at least one of a no-fly zone, a remote center of motion, and a velocity/force limit.

According to another embodiment of the system, the automation program is configured to join tissue by generating and sending commands to the surgical robot.

According to another embodiment of the system, the joining of the tissue is performed via suture, clips, staples or adhesive.

According to another embodiment of the system, the control module is further configured to implement visual servoing correction to bring the tool end portion to a target.

According to another embodiment of the system, the positions identified by the track processing module are three-dimensional positions.

Embodiments disclosed herein further provide for a computer implemented method of generating an automated surgical program. The method includes the steps of processing clinical data to produce a 3D spatial and temporal data of a surgery, obtaining surgical robot specifications and clinical parameters, generating the automated surgical program based on the 3D spatial and temporal data, the surgical robot specifications, and the clinical parameters.

According to another embodiment of the method, the clinical data includes at least one of visual data obtained from a camera or endoscope, kinematic data, or haptic data.

According to another embodiment of the method, the clinical data includes at least one of patient condition, vitals, and outcome of the surgery.

According to another embodiment of the method, the clinical data includes surgeon experience.

According to another embodiment of the method, the processing of the clinical data produces the 3D spatial and temporal data of the surgery based on considering correlations between tool motions and surgical outcomes.

According to another embodiment of the method, the processing of the clinical data produces the 3D spatial and temporal data of the surgery based on considering differences between surgeon experience levels to produce more effective movements According to another embodiment of the method, the 3D spatial and temporal data includes at least one of tool motion, tool positioning, location and movement of vital organs or structures, viable reference points, and tissue deformation.

According to another embodiment of the method, the surgical robot specifications include velocity and precision of the surgical robot.

According to another embodiment of the method, the generated automated surgical program includes surgical motions absent in clinical data but implementable by the surgical robot.

According to another embodiment of the method, the clinical parameters includes tissue characteristics.

According to another embodiment of the method, the tissue characteristics include expected movement and rigidity of the tissue or absorbability of dyes of the tissue.

According to another embodiment of the method, the automated surgical program includes: preferred movement patterns, critical operation information, a control module configured to instructs robot motions based on a combination of sensor information and the critical operation information.

According to another embodiment of the method, the critical operation information includes at least one of vital organ positions, reference points or markers, sensor data, and surgeon input.

According to another embodiment of the method, the control module is further configured to further generate the commands based on motion constraints that include at least one of remote center of motion, no-fly zones, and velocity limits.

According to another embodiment of the method, the control module is further configured to further generate the commands based on tissue deformation or movement models.

According to another embodiment of the method, wherein the automated surgical program is updatable with additional clinical data.

BRIEF DESCRIPTION OF THE DRAWINGS

FIGS. 5A and 5B show example infrared images with fluorescent markers, where FIG. 5A illustrates an infrared image with fluorescent markers and FIG. 5B illustrates a binary image with intensity threshold;

FIG. 6A illustrates the current image and FIG. 6B illustrates the target image;

FIG. 10A illustrates a visible spectrum image, FIG. 10B illustrates a NIR spectrum image, and FIG. 10C illustrates a visible image and NIR image overlaid;

FIG. 11A illustrates the biodegradable clip, the clasp, and the tissue and FIG. 11B illustrates how the clip pierces both tissues, and the clasp is tightened on one end of the clip to hold the tissues together;

DETAILED DESCRIPTION OF THE PREFERRED EMBODIMENTS

The embodiments of the invention describe a system for automation of surgical tasks. The embodiments consist of generating an automated surgical program based on clinical data, then applying the automated surgical program to patients during surgery.

Figure 1:
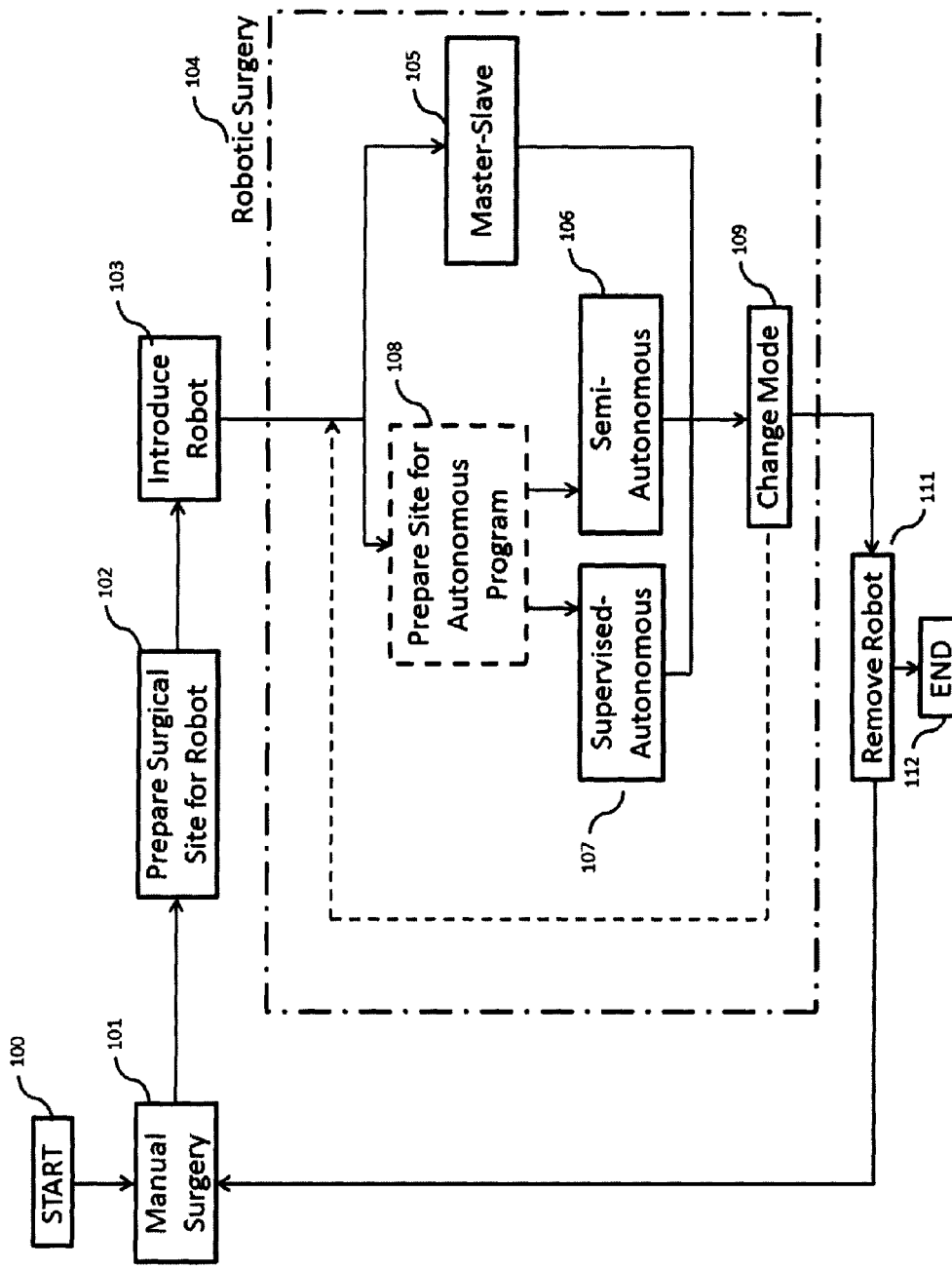
FIG. 1 shows the overall workflow of utilizing the invention in robotic surgery.

FIG. 1 shows the overall workflow of utilizing the proposed system in a surgical operation. The surgeon starts 100 the surgery by utilizing manual tools 101, either performing segments of the operation that can be done efficiently manually, or preparing the surgical site for the robot 102. Once the patient has been prepared, the surgeon then introduces the robot 103 into the patient, and begins the robotic mode of operation 104. When deployed, the robot may be set to work with one of three modes of operation: master-slave 105, where the surgeon controls the robot's motion directly through controllers; semi-autonomous 106, where the robot performs tasks under the direction of a surgeon; or supervised autonomous 107, where the robot performs a task autonomously under the supervision of the surgeon. Before activating the semi-autonomous or supervised autonomous mode of operation, the surgeon would prepare the surgical site and the surgical system as required 108. The surgeon may also freely switch between the different modes of operation 109, until the robot is no longer needed or must be removed to continue the surgery 111. After the robot's removal, the surgeon may either continue the surgery using manual tools 101, bringing the robot back if needed 103, or bring the operation to an end by performing any final tasks 112.

Figure 2:
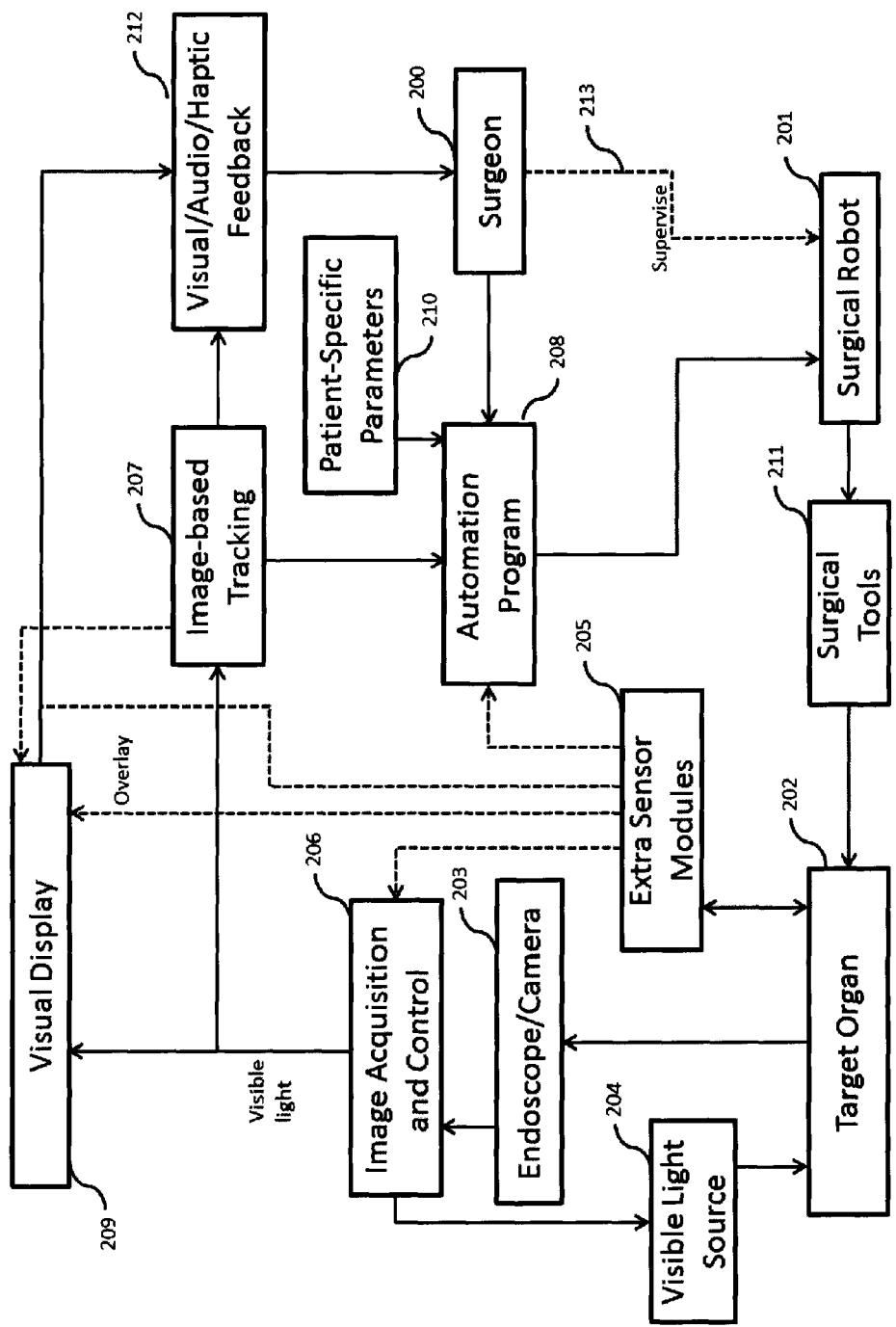
FIG. 2 shows the overall structure of the embodiment of the invention in semi-autonomous mode where the surgical tasks are partially automated.
Figure 3:
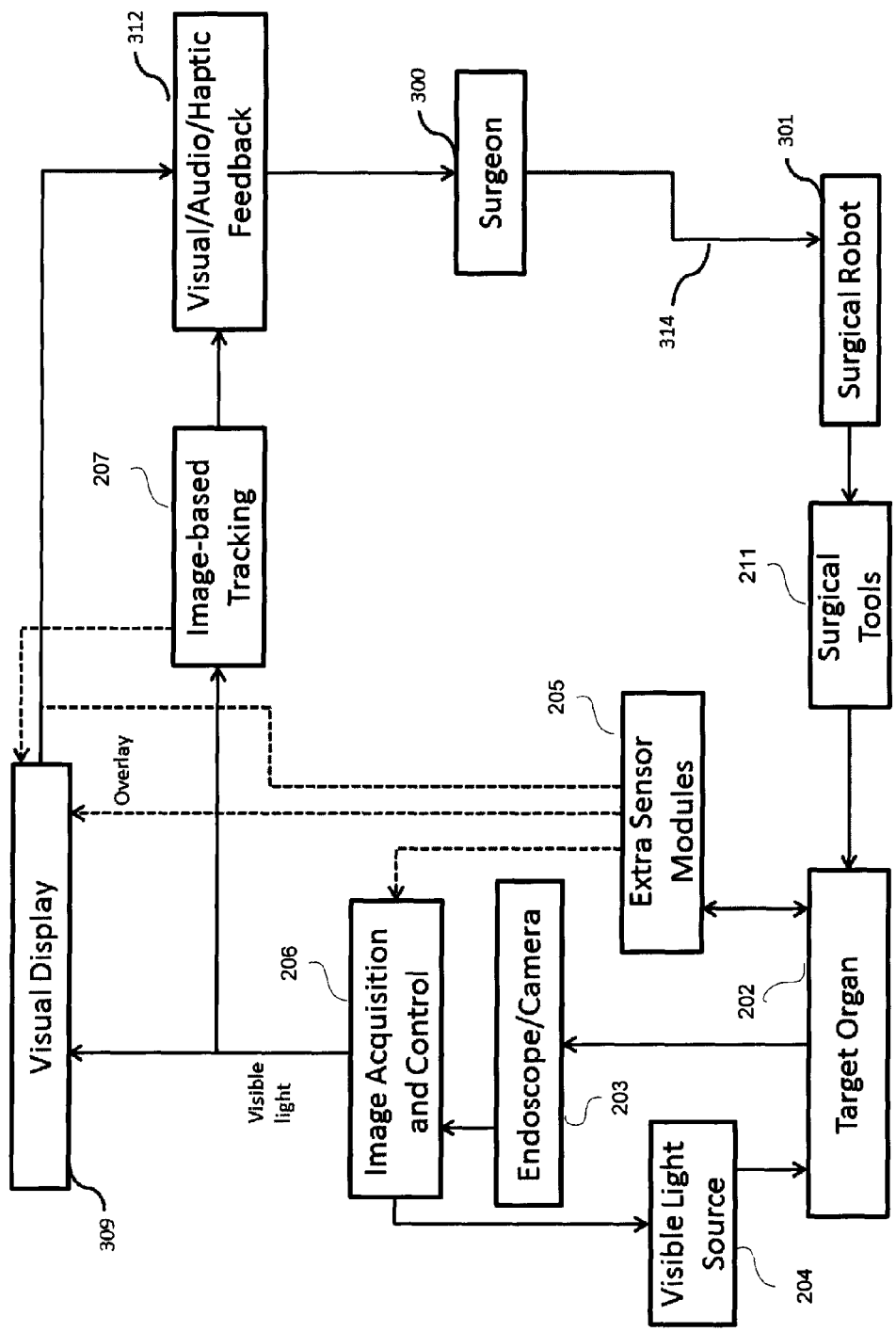
FIG. 3 shows the embodiment of the system in the master-slave robot-assisted mode.
Figure 4:
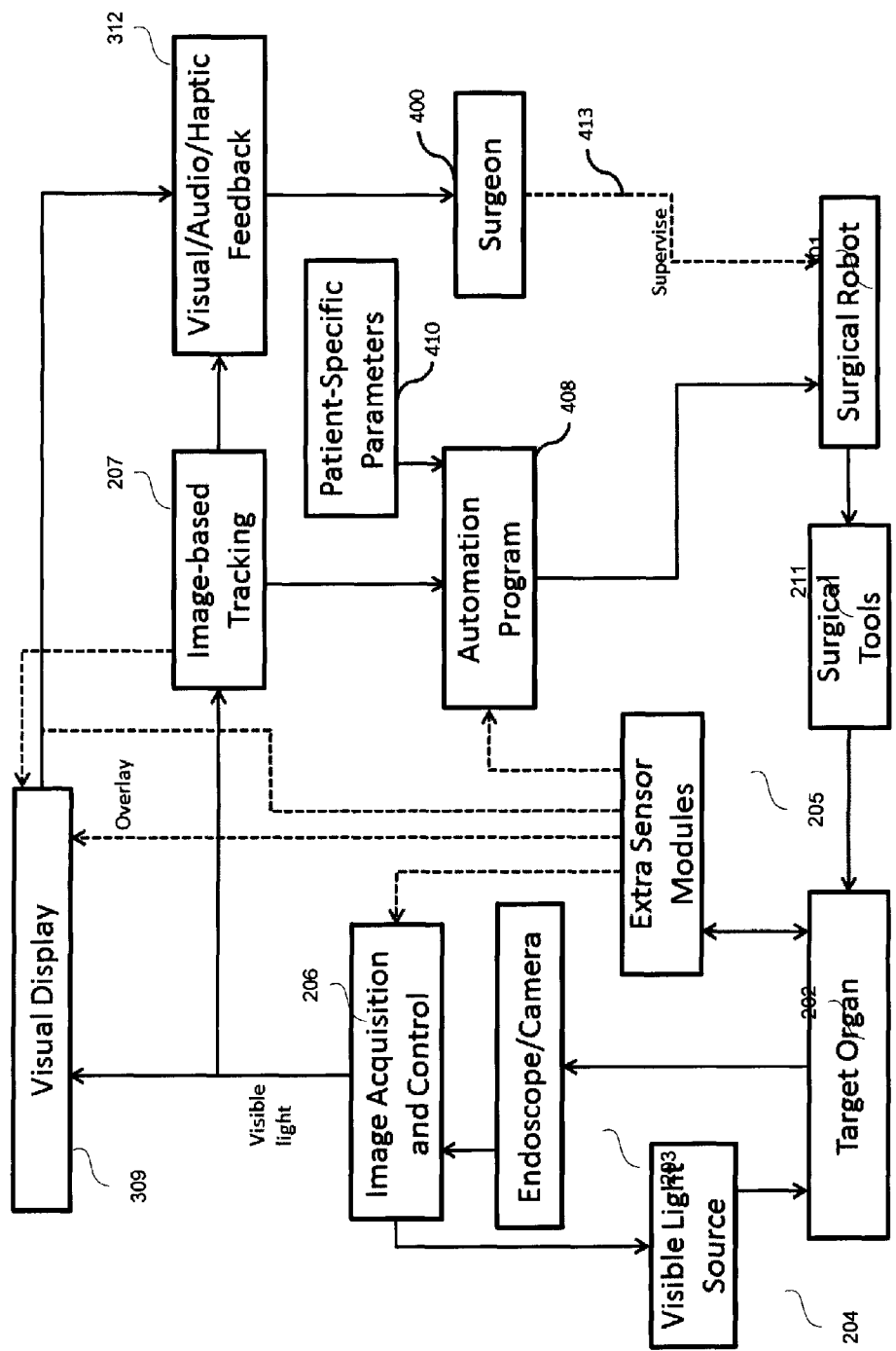
FIG. 4 shows an embodiment of the system with supervised autonomy.

FIGS. 2, 3 and 4 represent the different modes of the operation for the proposed system. In the semi-autonomous mode (FIG. 2) the surgeon 200 provides commands to the automation program 208 during the operation. The automation program 208 receives the tracking information from the image-based tracking module 207, combines the tracking information with the intraoperative commands from the surgeon 200 and the patient-specific parameters 210 and sends appropriate commands to the robot in real-time in order to control the surgical robot 201 and the surgical tool(s) 211 (which may or may not be specialized for the current procedure) to obtain a predetermined goal (e.g. anastomosis). The surgeon 200 can be given visual, audio or haptic feedback 212 while he/she is looking at the visual display 209, and interacts with the surgical robot as a supervisor 213, taking over control through a master console whenever required.

In master-slave mode (FIG. 3), the surgeon 300 controls the surgical tool through master-slave control 314 of a robot 301. The surgeon receives visual feedback through the visual display 309 and may also be provided with other visual, audio or haptic feedback 312 but the control loop is solely closed through the surgeon.

In supervised autonomous mode (FIG. 4), the control loop is solely closed via autonomous program 408 that utilizes image-based tracking and patient-specific parameters 410 except when the surgeon 400 stops the autonomous control and takes over control 413 to prevent a complication, correct for a wrong action, or other reasons.

In surgery, the surgeon must prepare the surgical scene using manual tools or the robot to enable the automation program to take over. This may include but is not limited to: placing the tools in the proximity of the target organ 202, moving the camera 203 to provide vision of the target organ 202, marking key reference points, setting up extra sensor modules 205, marking the work area, and marking the vital tissues/organs. Once the surgical scene is set up, the semi-autonomous and supervised autonomous modes of operation may be used as appropriate.

A visible light source 204 lights the surgical scene, allowing the camera 203 to record live images of the procedure. The image acquisition and control module 206 captures and digitizes the images from the endoscope/camera 203 and provides them to the image-based tracking module 207 and the visual display 209. The visual display 209 provides an image feed of the acquired visual images; the visual display 209 can also display an augmented reality image by overlaying the video with information from the extra sensors 205 or from the image-based tracking module 207. The image-based tracking module 207 applies image processing algorithms to track the tools and reference points. These tasks would be performed by a computer that is connected to the sensors and contains the software for image acquisition 206, automation program 208, image-based tracking module 207, and processing feedback 212.

The extra sensor modules 205, which are used as needed to make the automation program more robust, can send information from the extra sensor modules 205 to either the image acquisition module 206 or directly to the automation program 208, depending on the nature of the sensor. The extra sensor modules may also send information from the extra sensor modules 205 to the visual display 209 for overlaying with video or be sent to the surgeon console to provide visual, audio, or haptic feedback 212.

In one embodiment of the invention, the surgeon selects a series of automation programs from a library of available automation programs. An example of an automation program is one that performs a suturing task where one or more points on different tissues must be sutured or stitched together, that is, the surgical tool must be positioned with respect to the tissue to perform suturing.

In one embodiment of the invention, the automation program utilizes an image-based visual servoing system, where the robotic tool is controlled in closed-loop using an image-based control law. In visual servoing, the difference between the desired image, which depicts the tool at the target location, and the current image, which depicts the current tool and the target location, is used to compute the error in image coordinates. This error in image coordinates is used to generate the motion of the robotic tool towards the target position. As the robotic tool gets closer to the target location in the surgical field, the error in the image space gets smaller. At the final control loop iteration, the error approaches zero, at which point the tool has reached the target location in both the image coordinates and the Cartesian robot coordinates. This is the core of the image-based visual servoing control loop. If stereo camera system is used, the coordinates of the left and right images could be augmented to control more degrees of freedom (DOF) of the robotic tool.

One embodiment of the invention uses images that contain the visible spectrum of the surgical field and/or other non-visible light content such as near-infrared spectrum (NIR, 700~1100 nm). For example, before the autonomous program is activated, the surgeon may place NIR markers at target locations that will be tracked using an NIR camera. The distinguishability of the NIR markers from the visual spectrum images, along with the ability of near-infrared spectrum to pass through blood and tissue, allows for more robust real-time tracking of target tissues in the dynamic surgical environment (e.g. deforming soft tissue). Multi-spectral optical imaging may also be used to detect sub-surface tissue information that assist in optimal targeting.

Automation of anastomosis is described in an embodiment of this invention, where tubular organs such as the intestine are joined using sutures, clips, glue, or staples. In semi-autonomous anastomosis using sutures, the surgeon first prepares the tubular organs in pre-defined orientations and marks suture locations or circumference of tubes for the program to visually track. The automation program then autonomously moves the robotic tool to the selected suture locations and performs suturing. In autonomous anastomosis using sutures, the program first detects the optimal suture locations based on properties of the tissue (e.g. mechanical, optical, geometric) and kinematic and dynamic characteristics of the robotic tool for optimal dexterity. Once the optimal suture locations are detected, the autonomous program brings the tool to the suture location and performs suturing.

Figure 6B:
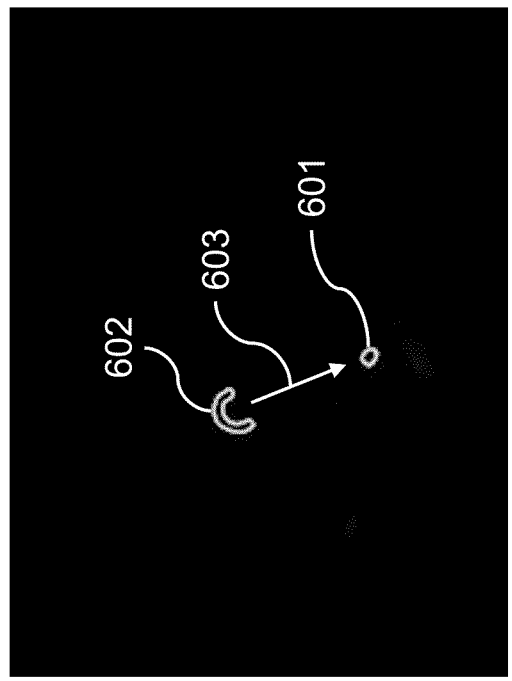
FIGS. 6A and 6B show example current and target images for use in visual servoing effecting image-coordinate error correction, where
Figure 6A:
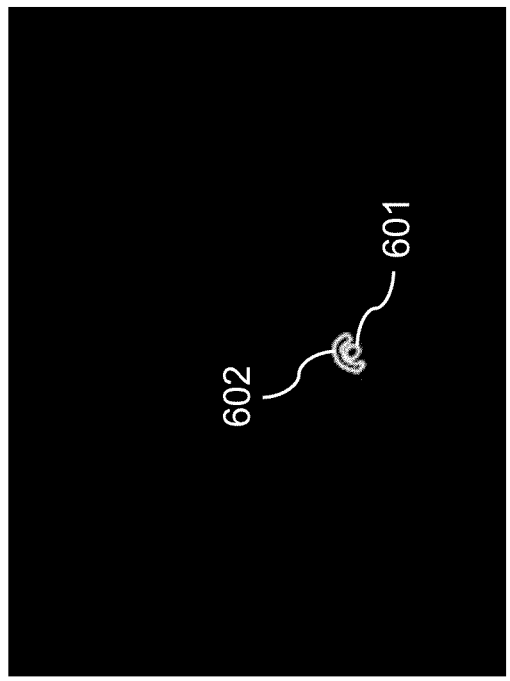

FIGS. 5 and 6 show one embodiment of this invention that utilizes visual servoing and NIR markers to perform anastomosis. In this embodiment, the surgeon places fluorescent NIR markers 500 at the target suture locations to prepare the surgical site for the autonomous program. The visual system obtains both visible spectrum and near-infrared spectrum images (FIG. 5A), allowing the visual servo to reliably track the NIR-marked tool 501 and suture locations 502 in real-time through the NIR markers 500. One example of image processing that may be performed to aid in tracking is an infrared-threshold binary image (FIG. 5B), which clearly differentiates the marked areas from the non-marked areas. The visual servo then moves 603 the robotic tool 602 towards the suture site 601 (FIG. 6A) so that the error in the image and Cartesian coordinate space approaches zero (FIG. 6B). Once a suture site is reached, the autonomous program places a suture before moving onto the next suture site.

To further aid in tracking of tissues in the dynamic and deforming surgical environment, certain embodiments of this invention may have means of obtaining 3D information about the surgical workspace. One embodiment of this means uses two cameras, which allows for the extraction of 3D depth information through a stereo triangulation algorithm. Another embodiment involves using structured-light 3D scanners to obtain 3D information. Another embodiment involves obtaining 3D information through light-field cameras.

Figure 7:
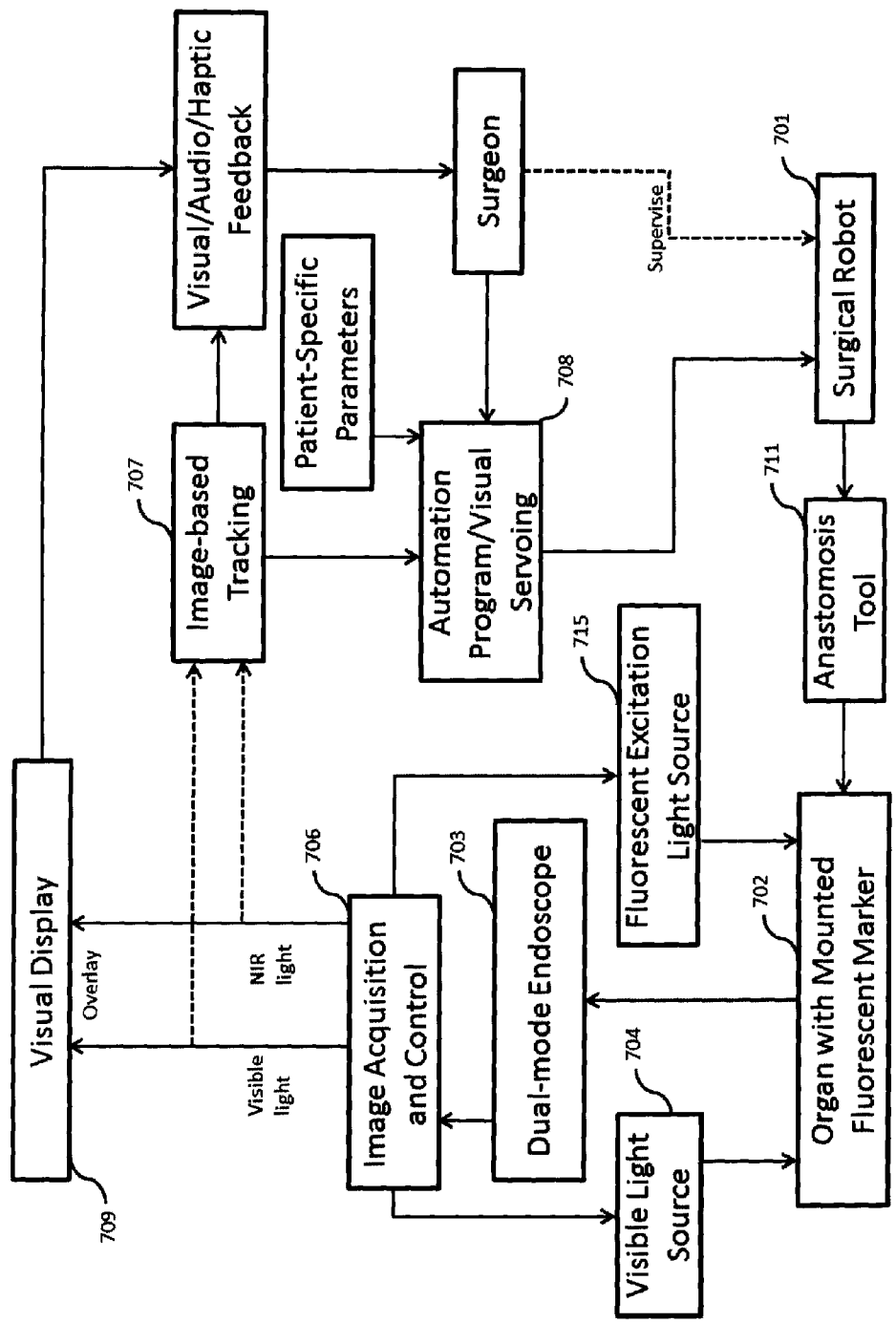
FIG. 7 shows an embodiment utilizing dual-mode endoscope for automation of anastomosis.

FIG. 7 shows the system diagram of the embodiment that utilizes visual servoing with NIR markers for anastomosis. Fluorescent markers are deployed on the organ 702 (e.g. two sides of a bile duct to be anastomosed) in manual mode and two light sources 704 and 715 illuminate the scene. One light source 704 is a visual light source that makes it possible to acquire normal images of the organs. The other light source 715 is a narrow-band source of light (e.g. in the near infrared range) that is chosen according to the excitation wavelength of the fluorescent material. Both visible light and fluorescent light images are captured by the dual-mode endoscope 703 and sent to the image acquisition and control module 706, which will then send the images to the visual display 709 for overlaying and to the image-based tracking module 707 for processing. The automation program's visual servoing control system 708 utilizes the fluorescent markings to become more robust, allowing the automation program to move the robot 701 and the specialized anastomosis tool 711 appropriately to carry out the desired procedure (anastomosis).

Figure 8:
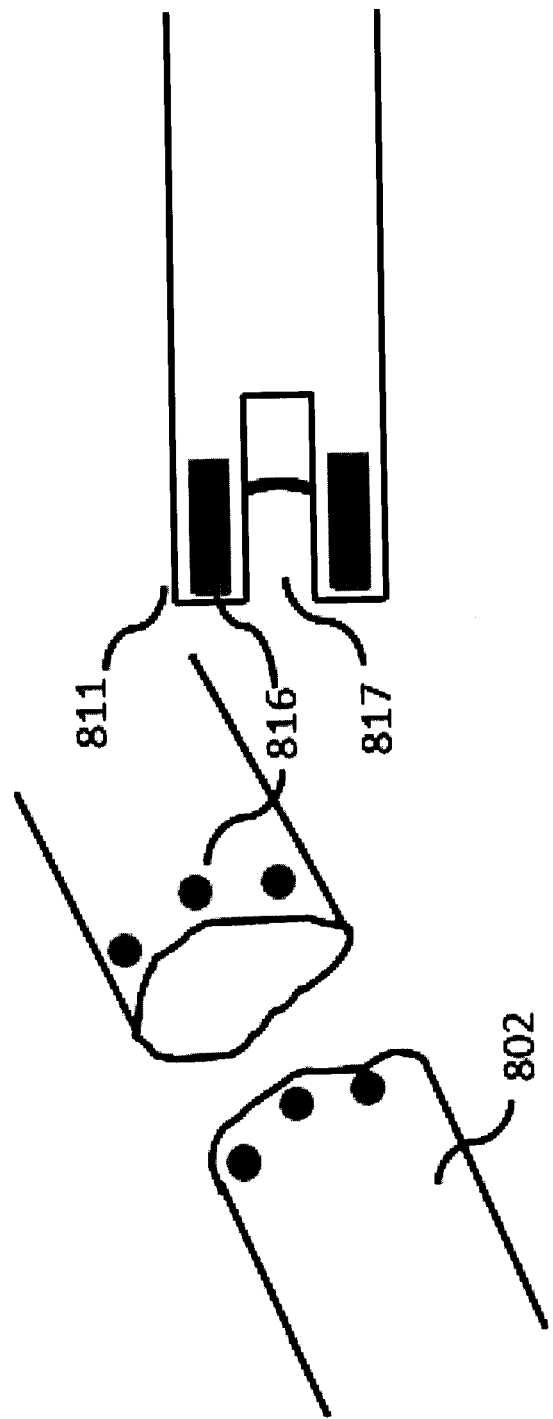
FIG. 8 shows how the tissue and tool may be marked with fluorescent markers with a view of an organ and an anastomosis tool for anastomosis with NIR and a biodegradable clip.
Figure 9:
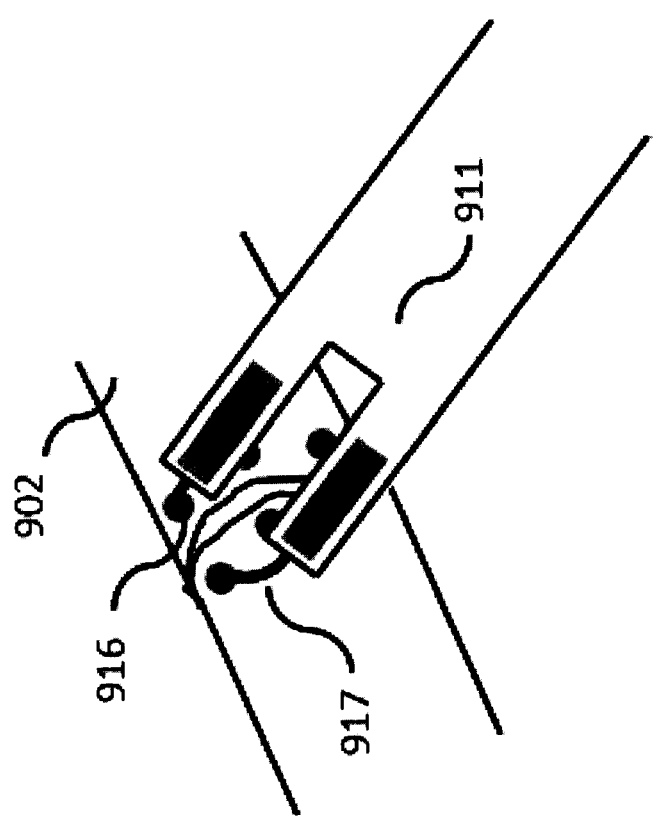
FIG. 9 shows how a specialized tool for automated anastomosis may work with a view of an anastomosis tool attaching a clip to the organ.
Figure 10C:
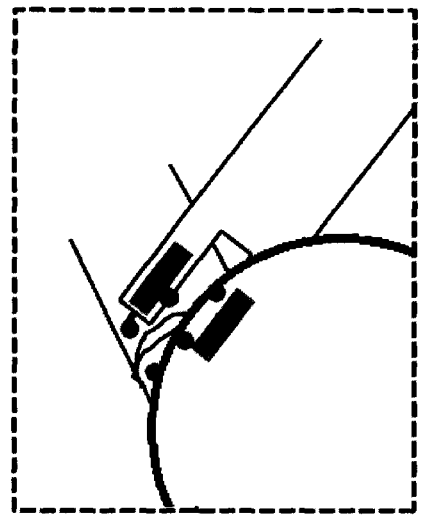
FIGS. 10A, 10B and 10C show the two images the dual-mode endoscope may receive, and how they may be overlaid, where
Figure 10B:
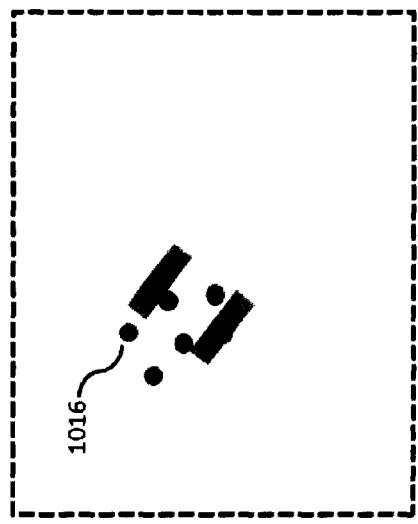
Figure 10A:
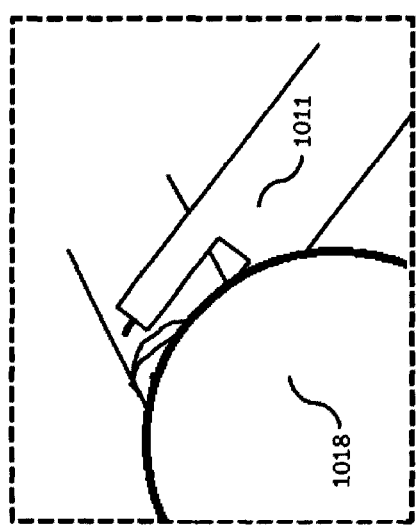

FIGS. 8, 9, and 10 show an embodiment of the invention that performs anastomosis with NIR markers and biodegradable clips. To prepare for the supervised autonomous mode of operation, fluorescent markers 816 are delivered around the anastomosis site 802, and optionally, the tool 811. The tool deploys biodegradable clips 817 (more detail is provided in FIG. 11) that can be used to perform the anastomosis. In FIG. 9, the autonomous program is provided with images of the fluorescent markers 916 that, along with other sensor data, are used to guide the tool 911 to the anastomosis site 902, where clips 917 will be deployed to perform the anastomosis. FIG. 10 demonstrates the potential benefit of using fluorescent markers in the presence of visual obstructions 1018 in the surgical field. While the obstruction would impair vision of the anastomosis site in the visible spectrum (FIG. 10A), certain fluorescent dyes emit infrared light that can pass through obstructions (FIG. 10B). By combining information from different spectrum of light (FIG. 10C), the visual tracking system is made more robust.

Figure 11A:
FIGS. 11A and 11B show an embodiment of a special clip made for anastomosis, where
Figure 11B:
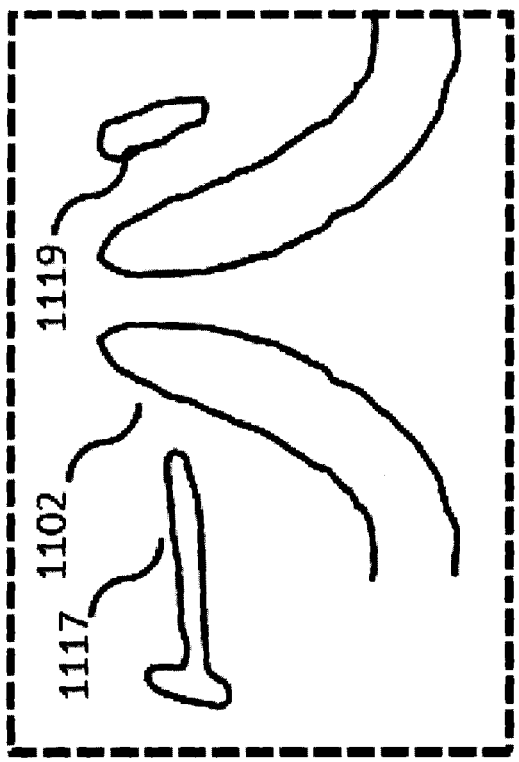

FIG. 11 shows one embodiment of a biodegradable clip 1117 used to perform the anastomosis. The clip pierces through the two tissues 1102 to be joined, and is fixed in place by tightening a biodegradable clasp 1119 around the tail of the biodegradable clip 1117.

Figure 12:
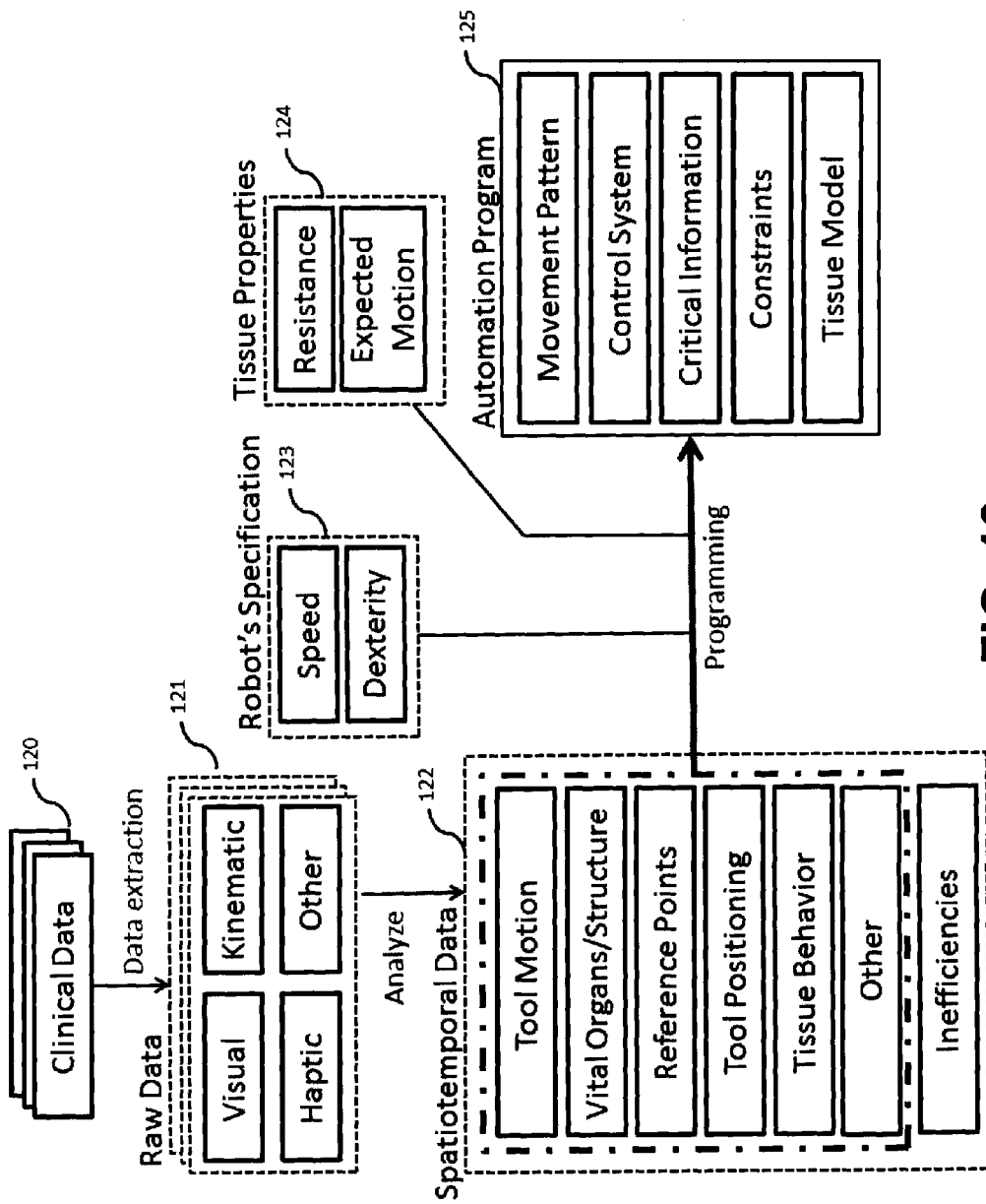
FIG. 12 shows the overall procedure for developing the automated surgical program from clinical data.

FIG. 12 represents the general workflow for developing the automated surgical program from clinical data. Clinical data 120 is processed to obtain a set of raw data 121. This consists of visual data from cameras or endoscopes, kinematic and haptic information if the surgery is performed robotically, and other relevant data, such as the patient's condition throughout the surgery, outcome, vitals, etc. These data are analyzed, either manually or by using computer algorithms such as pattern recognition, to produce a set of spatiotemporal information 122 about the surgery. This set contains tool motion, tool positioning, location and movement of vital organs/structures, viable reference points, tissue deformation, and other information, such as correlation between certain motions and patient outcomes. Inefficient movements can also be identified at this stage by comparing the movements of surgeons of varying experience, which can be removed during programming and identified for training surgeons in the future. This may be realized by techniques from robotic imitation-learning, where sensory data from expert operators are gathered while performing similar maneuvers. The sensory data, such as trajectories of the input device, are first scaled and normalized, then parameterized. The parameters are learned, e.g., using linear subspace methods such as Principle Component Analysis (PCA) from maneuver repetitions of the same task. Each expert maneuver can then be represented by linear combinations of different parametric curves. The movements may be further optimized by incorporating movements that surgeons would normally not make due to dexterity constraints of their hands. This spatiotemporal data of the procedure is then combined with the surgical robot's capability 123 (e.g. speed and dexterity) and tissue characteristics 124 (e.g. expected movement, tissue rigidity) to produce the automation program 125 specific to a surgical procedure. The program consists of the movement patterns in the procedure, a control system that combines different sensory information to produce the movement patterns, a set of critical information (e.g. reference points, vital organs/vessels) that must be provided, a set of constraints, such as speed limits and spatial constraints, and deformation/movement models of the tissues involved. An updating method may also be implemented to incorporate more expert surgeons' clinical data to help improve this automated procedure over time. Each of the program or algorithm based elements of the above noted description can be implemented by hardware such as the hardware found in the description of FIG. 13. In FIG. 12, the computer 1299 includes a CPU 1200 which performs the processes described above. The process data and instructions may be stored in memory 1202. These processes and instructions may also be stored on a storage medium disk 1204 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the system communicates, such as a server or computer.

Further, the claimed advancements may be provided as a utility application, background daemon, or component of an operating system, or combination thereof, executing in conjunction with CPU 1200 and an operating system such as Microsoft Windows 7, UNIX, Solaris, LINUX, Apple MAC-OS and other systems known to those skilled in the art.

CPU 1200 may be a Xenon or Core processor from Intel of America or an Opteron processor from AMD of America, or may be other processor types that would be recognized by one of ordinary skill in the art. Alternatively, the CPU 1200 may be implemented on an FPGA, ASIC, PLD or using discrete logic circuits, as one of ordinary skill in the art would recognize. Further, CPU 1200 may be implemented as multiple processors cooperatively working in parallel to perform the instructions of the inventive processes described above.

Figure 13:
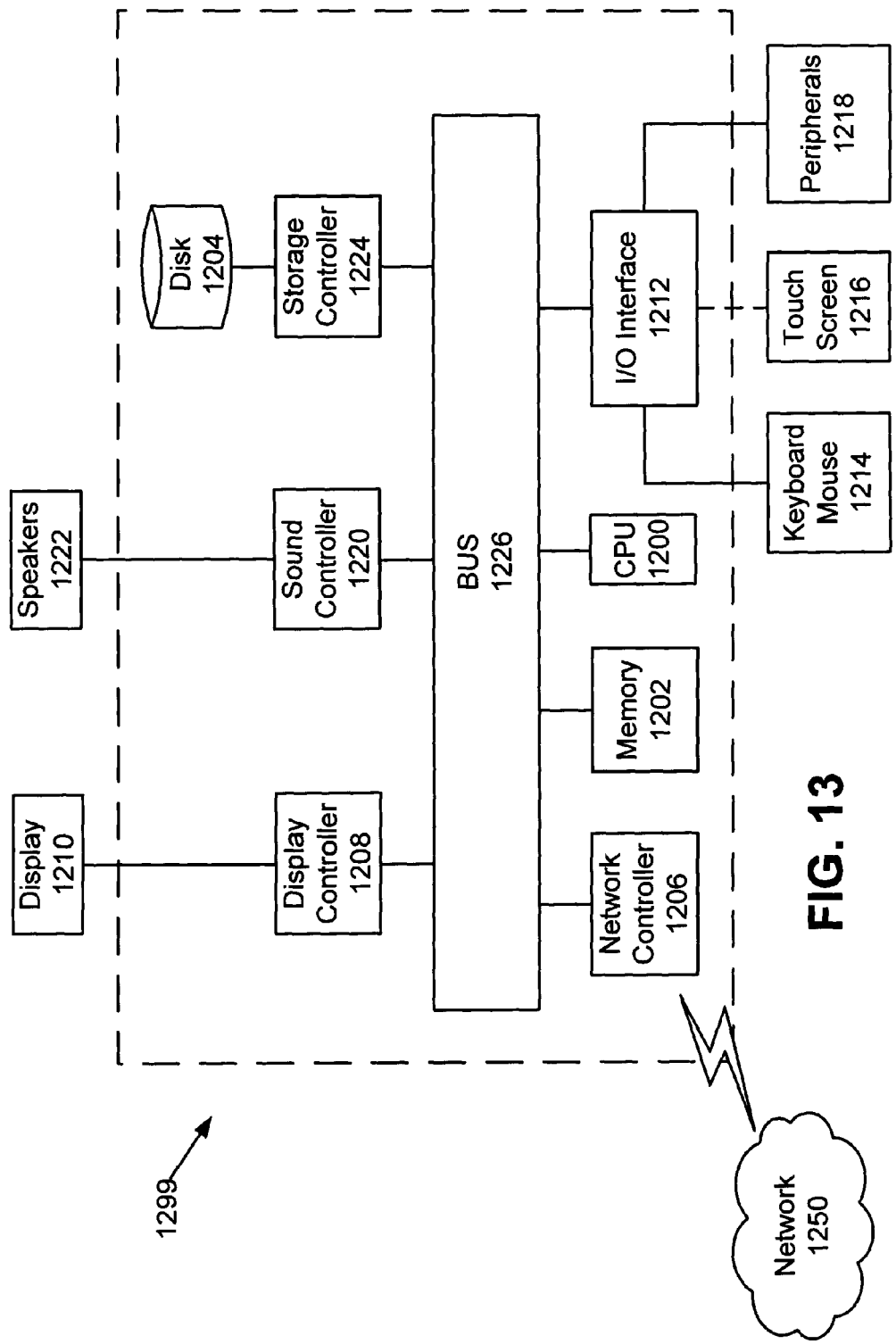
FIG. 13 illustrates a block diagram of a computing device according to one embodiment.

The computer 1299 in FIG. 13 also includes a network controller 1206, such as an Intel Ethernet PRO network interface card from Intel Corporation of America, for interfacing with network 1250. As can be appreciated, the network 1250 can be a public network, such as the Internet, or a private network such as an LAN or WAN network, or any combination thereof and can also include PSTN or ISDN sub-networks. The network 1250 can also be wired, such as an Ethernet network, or can be wireless such as a cellular network including EDGE, 3G and 4G wireless cellular systems. The wireless network can also be WiFi, Bluetooth, or any other wireless form of communication that is known.

The computer 1299 further includes a display controller 1208, such as a NVIDIA GeForce GTX or Quadro graphics adaptor from NVIDIA Corporation of America for interfacing with display 1210, such as a Hewlett Packard HPL2445w LCD monitor. A general purpose I/O interface 1212 interfaces with a keyboard and/or mouse 1214 as well as a touch screen panel 1216 on or separate from display 1210. General purpose I/O interface also connects to a variety of peripherals 1218 including printers and scanners, such as an OfficeJet or DeskJet from Hewlett Packard. The peripheral elements previously described in the above exemplary embodiments may be embodied by the peripherals 1218 in the exemplary embodiment of FIG. 13.

A sound controller 1220 may also be provided in the computer 1299, such as Sound Blaster X-Fi Titanium from Creative, to interface with speakers/microphone 1222 thereby providing sounds and/or music. The speakers/microphone 1222 can also be used to accept dictated words as commands for controlling the robot-guided medical procedure system or for providing location and/or property information with respect to the target property.

The general purpose storage controller 1224 connects the storage medium disk 1204 with communication bus 1226, which may be an ISA, EISA, VESA, PCI, or similar, for interconnecting all of the components of the robot-guided medical procedure system. A description of the general features and functionality of the display 1210, keyboard and/or mouse 1214, as well as the display controller 1208, storage controller 1224, network controller 1206, sound controller 1220, and general purpose I/O interface 1212 is omitted herein for brevity as these features are known.

Obviously, numerous modifications and variations of the present disclosure are possible in light of the above teachings. It is therefore to be understood that within the scope of the appended claims, the invention may be practiced otherwise than as specifically described herein. For example, advantageous results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable processing circuits configured to execute program code and/or computer instructions to execute the functions, processes and algorithms described herein. A processing circuit includes a programmed processor, as a processor includes circuitry. A processing circuit also includes devices such as an application specific integrated circuit (ASIC) and conventional circuit components arranged to perform the recited functions.

The functions and features described herein may also be executed by various distributed components of a system. For example, one or more processors may execute these system functions, wherein the processors are distributed across multiple components communicating in a network. The distributed components may include one or more client and/or server machines, in addition to various human interface and/or communication devices (e.g., display monitors, smart phones, tablets, personal digital assistants (PDAs)). The network may be a private network, such as a LAN or WAN, or may be a public network, such as the Internet. Input to the system may be received via direct user input and/or received remotely either in real-time or as a batch process. Additionally, some implementations may be performed on modules or hardware not identical to those described. Accordingly, other implementations are within the scope that may be claimed.

It should be noted that, as used in the specification and the appended claims, the singular forms "a," "an," and "the" include plural referents unless the context clearly dictates otherwise.

What is claimed is:

1. A system for performing an automated surgical procedure, comprising:
   a sensor that provides information regarding a surgical field;
   a user interface configured to receive commands issued by a surgeon;
   a feedback device configured to relay information to the surgeon;
   a surgical tool having an end portion used for performing a surgical task;
   a surgical robot that is coupled to the surgical tool and that positions and orients the surgical tool;
   a track processing module implemented by processing hardware and configured to receive sensor data from the sensor,
      identify distinct points on at least two of a target tissue, surrounding tissues and the surgical tool end portion based on the sensor data, and
      generate tracking information by tracking the identified distinct points on the respective at least two of the target tissue, the surrounding tissues and the surgical tool end portion, the tracking including identifying a location of the identified distinct points with respect to a reference position over time even when the identified distinct points move with respect to the reference position; and
   a control module implemented by the processing hardware and configured to process the surgical field information received from the sensor, the tracking information received from the track processing module, and the commands received from the user interface using an automation program, to generate commands for the surgical robot based on the processing, and to send the commands to the surgical robot.

2. The system according to claim 1, wherein the system comprises a plurality of sensors that provide information regarding the surgical field.

3. The system according to claim 1, wherein the sensor is one of a camera, a near-infrared fluorescent (NIR) camera, a depth camera, a structured light 3D scanner.

4. The system according to claim 1, wherein the feedback device is a display configured to show visual cues or images or an auditory device.

5. The system according to claim 1, wherein the track processing module is further configured to track the identified distinct points in at least one of the target tissue, the surrounding tissues and the surgical tool end portion, using near-infrared fluorescent (NIR) markers.

6. The system according to claim 1, wherein the surgical robot is detachably coupled to the surgical tool.

7. The system according to claim 1, wherein the automation program is semi-autonomous.

8. The system according to claim 1, wherein the automation program is supervised autonomous.

9. The system according to claim 1, wherein the control module is configured to disable the automation program and implement a master-slave mode based on surgeon input.

10. The system according to claim 1, wherein the control module is further configured to implement visual servoing correction.

11. The system according to claim 1, wherein the automation program is configured to implement anastomosis.

12. The system according to claim 1, wherein the control module is further configured to further generate the commands based on at least one of a no-fly zone, a remote center of motion, and a velocity/force limit.

13. The system according to claim 1, wherein the automation program is configured to join tissue by generating and sending commands to the surgical robot.

14. The system according to claim 13, wherein the joining of the tissue is performed via suture, clips, staples or adhesive.

15. The system according to claim 1, wherein the control module is further configured to implement visual servoing correction to bring the tool end portion to a target.

16. The system according to claim 1, wherein the distinct points identified by the track processing module are three-dimensional positions.

17. The system according to claim 1, wherein the track processing module is further configured to identify positions in each of the target tissue, the surrounding tissues and the surgical tool end portion based on the sensor data.

18. The system according to claim 17, wherein the track processing module is further configured to generate tracking information by tracking the identified distinct points in each of the target tissue, the surrounding tissues and the surgical tool end portion.

19. The system according to claim 17, wherein the track processing module is further configured to generate tracking information by tracking the identified positions in each of the target tissue, the surrounding tissues and the surgical tool end portion using fluorescent dyes that emit infrared light which pass through organic obstructions within the surgical field.

20. The system according to claim 1, wherein the surgical robot is coupled to a movement mechanism that moves the surgical robot in and out of the surgical field.

21. The system according to claim 1, wherein the control module is configured to interrupt the automation program based on surgeon input.

22. The system according to claim 1, wherein the target tissue and the surrounding tissues are each soft tissue.

23. The system according to claim 1, further comprising:
   a plurality of sensors that provide information regarding the surgical field wherein the plurality of sensors include at least two of a camera, a near-infrared fluorescent (NIR) camera, a depth camera, a structured light 3D scanner.

24. The system according to claim 1, wherein the track processing module is further configured to track the identified distinct points in at least one of the target tissue and the surrounding tissues using fluorescent dye applied to a position on the respective tissue.

25. The system according to claim 1, wherein the control module is further configured to update commands for the surgical robot based on updated surgical field information received from the sensor and updated tracking information received from the track processing module.

26. The system according to claim 1, wherein the control module is further configured to generate the commands based on a no-fly zone which is defined by selected ones of the distinct points on the target tissue or the surrounding tissue, which move with respect to the reference position based on movement of the respective one of the target tissue or the surrounding tissue.

* * * * *